United States Patent [19]
Waltuck et al.

[11] 4,367,015
[45] Jan. 4, 1983

[54] CONTROL MEANS FOR OPTICAL INSTRUMENTATION

[75] Inventors: Morey H. Waltuck, Worcester, Mass.; David L. Guyton, Baltimore, Md.

[73] Assignee: Warner Lambert Technologies, Inc., Southbridge, Mass. ; a part interest

[21] Appl. No.: 202,267

[22] Filed: Oct. 30, 1980

[51] Int. Cl.³ .................... G02B 13/08; G02B 15/00
[52] U.S. Cl. ................................. 350/429; 350/420; 350/433; 351/200
[58] Field of Search ................ 350/420, 429, 433; 351/1, 6

[56] References Cited

U.S. PATENT DOCUMENTS

| | | | |
|---|---|---|---|
| 4,043,641 | 8/1977 | Gottlieb | 350/181 |
| 4,117,341 | 9/1978 | Persson | 351/6 X |
| 4,179,196 | 12/1979 | Persson et al. | 351/30 |
| 4,185,896 | 1/1980 | Buhler | 351/29 |
| 4,203,651 | 5/1980 | Persson | 350/181 |

Primary Examiner—John K. Corbin
Assistant Examiner—Rodney Bovernick
Attorney, Agent, or Firm—Alan H. Spencer

[57] ABSTRACT

In an ophthalmic refractor system for determining cylinder power and direction of axis for visual correction, cylinder axis orientation based upon corrective cylinder power in the refractor viewing path is automatically determined and introduced into the system.

4 Claims, 3 Drawing Figures

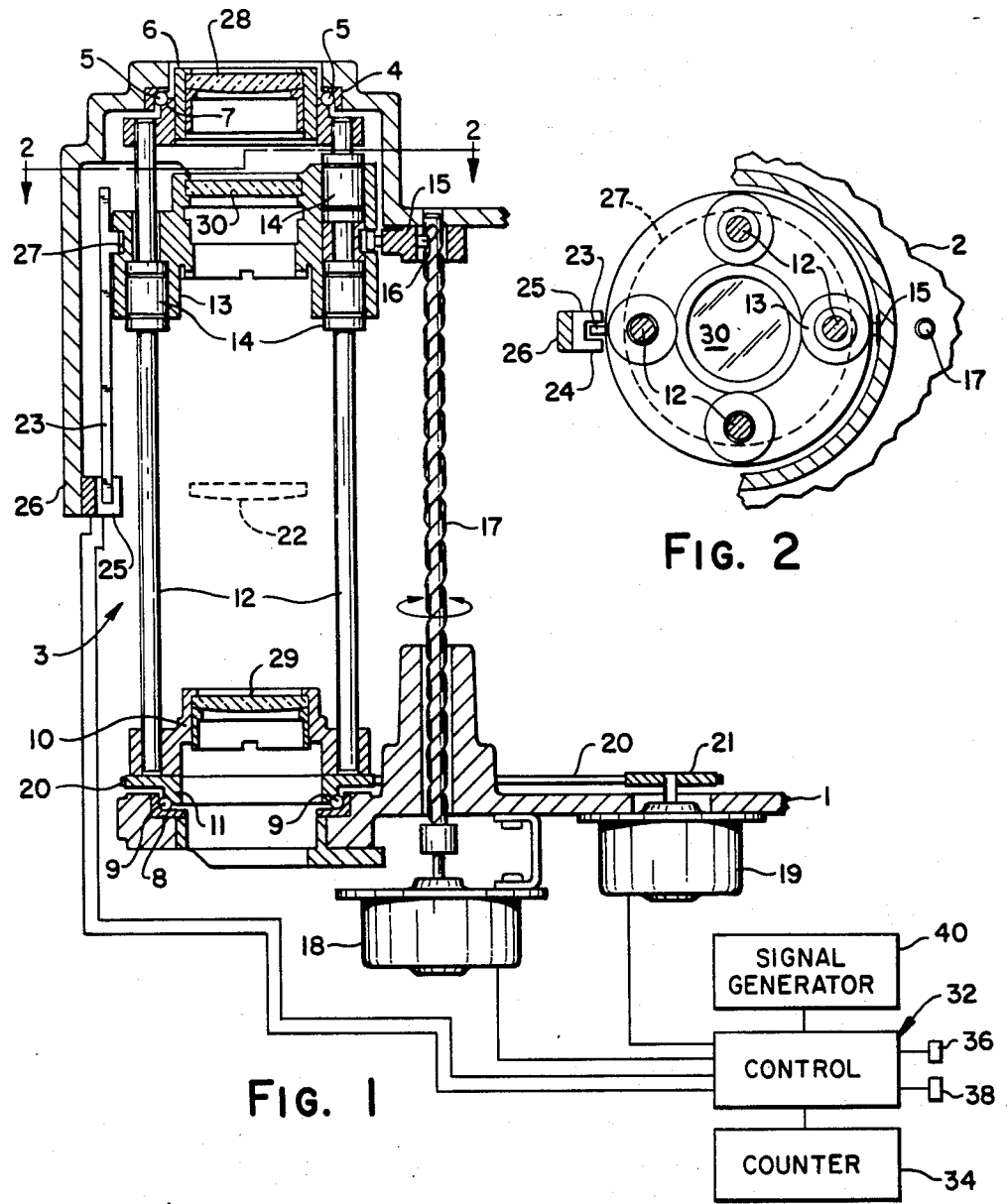

CONTROL MEANS FOR OPTICAL INSTRUMENTATION

BACKGROUND OF THE INVENTION

1. Field of the Invention

This invention relates to control means for optical instruments and has particular reference to apparatus for automatically adjusting amount of axial change required in an astigmatic refraction finding.

2. Discussion of the Prior Art

Traditionally in refracting eyes, refinement of the axis of the corrective cylinder power is accomplished by using a cross cylinder lens which has a fixed axial relationship to the corrective cylinder power. This cross cylinder lens is flipped about an axis to determine the best visual clarity. The operator interprets the response of the patient by arbitrarily increasing or decreasing the axis of the corrective cylinder power a fixed amount or an amount intuitively interpreted based on the corrected cylinder power and experience.

The present invention avoids reliance upon the operator for determination of amount for which axis of the correcting cylinder lens is changed and, accordingly, there is the object of automatically effecting the change of cylinder axis required for patient correction based upon the amount of corrective cylinder power in the viewing path.

More particularly, there is the aforesaid object of obviating reliance upon operator experience and intuitiveness in adjusting axis of corrective cylinder power.

Other objects and advantages of the invention will become apparent from the following description.

SUMMARY OF THE INVENTION

In ophthalmic refractor apparatus for determining cylinder power and direction of axis necessary for visual correction, the present invention provides control means for adjusting cylinder axis. The control means is constructed and arranged to automatically determine and effect adjustment of direction of cylinder axis according to the amount of corrective cylinder power in the patient's viewing path.

U.S. Pat. Nos. 4,043,641; 4,179,196; 4,117,341 and 4,203,651 exemplify refracting systems to which the present invention has particular applicability.

Details of the invention will become more readily apparent from the following description when taken in conjunction with the accompanying drawings.

IN THE DRAWINGS

FIG. 1 diagramatically illustrates ophthalmic refractor apparatus incorporating an embodiment of the present invention;

FIG. 2 is a cross-sectional view of the apparatus of FIG. 1 taken approximately along line 2—2; and FIG. 3 is a graphic representation of signal level generated by a detector in the system of FIGS. 1 and 2.

DESCRIPTION OF THE PREFERRED EMBODIMENTS

Referring to the apparatus of FIG. 1, there is shown a device having a frame with lower frame portion 1 and upper frame portion 2 and optical assembly designated generally by 3. The upper frame portion 2 has outer race 4 positioned therein. Ball bearings 5 rotatably support upper lens mount 6 by inner race 7. Lower frame portion 1 supports outer race 8. Ball bearings 9, in conjunction with outer race 8, rotatably positions lower lens mount 10 by inner race 11. Shafts 12 connect upper lens mount 6 and lower lens mount 10 to maintain a fixed spacing therebetween and join the lens mounts for concurrent rotation thereof. Carriage 13 is slidably mounted by bearings 14 on shafts 12. Follower 15 has pin 16 operatively engaging threaded shaft 17. Threaded shaft 17 is rotated in either direction by cylinder motor 18 to selectively move carriage 13 along shafts 12. Axis motor 19 rotates optical assembly 3 via belt 20 and pulley 21 to selectively position the principal meridians.

The apparatus described above carries a pair of cylinder lenses 28 and 29 having a combined focal power in a principal meridian. Cylinder lens 30 has a cylinder power equal to the combined cylinder power of lenses 28 and 29 in a principal meridian normal to the principal meridian of lenses 28 and 29. The focal power in the principal meridian of cylinder lens 30 is varied by movement of carriage 13 along shafts 12. A reference position 22 designates the location of cylinder lens 30 when the focal power in both principal meridians is the same. As cylinder lens 30 moves away from reference position 22 the power along its principal meridian is continuously increased.

It is frequently desirable to be able to return a member movable in either direction along a path to a reference position. Referring again to FIG. 1, reference position 22 represents a chosen position to which it is frequently desired to return lens 30. Occluder 23 is connected to follower 15 which engages groove 27 in carriage 13 to permit rotation of optical assembly 3. Occluder 23 extends parallel to the path travelled by carriage 13 along shafts 12. An energy beam such as that from IR emitter 25 is positioned on support 26 adjacent to the path travelled by occluder 23. Detector 24 is positioned by support 26 on the opposite side of the path travelled by occluder 23. The energy beam emitted by IR emitter 25 is blocked by occluder 23, if cylinder lens 30 is above reference position 22. If cylinder lens 30 is below reference position 22, detector 24 produces a signal generated by the unoccluded light beam. FIG. 3 is a graphic representation of the signal produced by detector 24 plotted against the position of cylinder lens 30. When cylinder lens 30 is positioned above reference position 22 and the control is activated to return cylinder lens 30 to the reference position, the control means 32 will direct motor 18 to rotate counter clockwise because the light beam is blocked by occluder 23 until detector 24 receives light from emitter 25. A signal indicating light is being received by detector 24 which causes control 32 to stop motor 18. When cylinder lens 30 is below reference position 22 and the control is activated to return cylinder lens 30 to the reference position, the presence of a signal from detector 24 is acted upon by the control to direct motor 18 to run clockwise driving cylinder lens 30 toward reference position 22. As soon as the light beam from IR emitter 25 is interrupted by occluder 23 control 32 stops motor 18. Thus, activation of control 32 will directly return cylinder lens 30 to the reference position from any position of carriage 13 along shafts 12.

Rotational adjustment of optical assembly 3 by motor 19 for select positioning of cylinder axis direction according to amount of corrective cylinder power in the viewing path of the FIG. 1 apparatus is accomplished by the addition to control 32 of counter 34 (random access memory, RAM) which is adapted to temporarily store information of position of cylinder lens 30 when adjustment up or down from position 22 is made with motor 18 to a visual cylinder power correction. For example, with cylinder motor 18 being operated in steps, counting and storage of motor steps from reference position 22 is memory stored in counter 34 for subsequent use in determining optimum extent of rotation of assembly 3 for cylinder axis alignment.

Stepping buttons 36 and 38 are arranged on control 32 for effecting operation of axis motor 19 in opposite directions as needed. These directions are modified by the signal of FIG. 3, being reversed when position of cylinder lens 30 passes through position 22. For example, button 36 may be actuated for clockwise rotation of assembly 3 and button 38 for counter-clockwise rotation or vice versa. If the above condition exists when lens 30 is above position 22, it is reversed when lens 30 is below position 22 or vice versa.

Also incorporated in control 32 is signal generator 40 which, in conjunction with counter 34, provides signals to motor 19 which are so adjusted as to actuate motor 19 a predetermined number of steps (rotational angle) according to the distance and direction of cylinder lens 30 from its reference position 22. For greater amounts of cylinder power (Diopters) afforded by the positioning of lens 30, smaller amounts (degrees) of rotation of assembly 3 are effected and vice versa.

The system of control 32 including generator 40 and counter 34 recalls the counter 34 stored cylindrical power and determines the required amount of corrective motion as illustrated in the following exemplary table:

| DIOPTERS | DEGREES |
| --- | --- |
| 0 to less than 1 | 10 |
| 1 to less than 2 | 5 |
| 2 to less than 3 | 3 |
| 3 to less than 5 | 2 |
| 5 to 8 | 1 |

The above operation is repeated until the patient indicates that the best cylinder axis has been reached.

Those interested in details of prior art cross-cylinder testing for location of cylinder axis in patient refraction may refer to U.S. Pat. No. 4,185,896.

The artisan will readily appreciate that modifications or other adaptations of the present embodiment of the invention may be made to suit particular requirements, i.e. use on instruments other than that of the present illustration. Accordingly, all modifications of the invention which incorporate the above concept are to be considered as coming within the scope of the following claims or range of equivalency to which they are entitled.

We claim:

1. In an optical instrument for automatically adjusting amount of axial change required in an astigmatic finding wherein said instrument has variable cylinder lens means for evaluation of astigmatic visual errors, first drive means for changing the effective power of said cylinder lens means, second drive means for changing the effective cylinder axis of said lens means and control means for selectively actuating said first and second drive means wherein the improvement comprises: counter means to generate a first signal of a level representative of adjustment of cylinder power of said variable cylinder lens and store said first signal; and actuating signal generator means for producing a signal to said second drive means for changing cylinder axis according to said stored signal.

2. The improvement in an optical instrument according to claim 1 including actuating means associated with said control means for manually selectively initiating said cylinder axis adjustment, the amount of adjustment being automatically restricted to that permitted by said stored first signal.

3. The improvement in an optical instrument according to claim 2 wherein said cylinder axis adjustment in rotational degrees corresponds to said adjustment of cylinder power (Diopters) approximately according to the following table:

| DIOPTERS | DEGREES |
| --- | --- |
| 0 to less than 1 | 10 |
| 1 to less than 2 | 5 |
| 2 to less than 3 | 3 |
| 3 to less than 5 | 2 |
| 5 to 8 | 1 |

4. The improvement in an optical instrument according to claim 2 wherein said actuating means includes a pair of buttons, one adapted to initiate said cylinder axis adjustment for one direction of axis rotation when actuated and the other of said buttons being adapted to initiate an opposite direction of cylinder axis rotation.

* * * * *